United States Patent
Benedetti

(10) Patent No.: US 11,619,641 B2
(45) Date of Patent: Apr. 4, 2023

(54) SAMPLE CONTAINER CARRIER WITH DATA CARRIER FOR AN IN-VITRO DIAGNOSTICS SYSTEM

(71) Applicant: Roche Diagnostics Operations, Inc., Indianapolis, IN (US)

(72) Inventor: Riccardo Leone Benedetti, Fehraltorf (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 359 days.

(21) Appl. No.: 17/075,821

(22) Filed: Oct. 21, 2020

(65) Prior Publication Data
US 2021/0123934 A1    Apr. 29, 2021

(30) Foreign Application Priority Data
Oct. 24, 2019    (EP) .................................... 19204997

(51) Int. Cl.
*G01N 35/00* (2006.01)
*G16H 50/20* (2018.01)

(52) U.S. Cl.
CPC ....... *G01N 35/00732* (2013.01); *G16H 50/20* (2018.01); *G01N 2035/00801* (2013.01); *G01N 2035/00831* (2013.01)

(58) Field of Classification Search
CPC ... G01N 35/00732; G01N 2035/00801; G01N 2035/00831; G01N 35/04;
(Continued)

(56) References Cited

U.S. PATENT DOCUMENTS 6,343,690 B1    2/2002  Britton et al.
2004/0267403 A1    12/2004  Itoh
(Continued)

FOREIGN PATENT DOCUMENTS

CN    107703317 A    2/2018
CN    108927239 A    12/2018
(Continued)

*Primary Examiner* — Jill A Warden
*Assistant Examiner* — John McGuirk
(74) *Attorney, Agent, or Firm* — Roche Diagnostics Operations, Inc.

(57) ABSTRACT

A container carrier for carrying a sample container along a track is presented. The container carrier comprises a holding portion for receiving and holding a sample container and a base portion. A radio frequency identification (RFID) tag containing identifying information is provided with an antenna for wireless communication of the RFID tag with a reader device of the diagnostics system to read the identifying information. The RFID tag is on the holding portion. An arrangement for a diagnostics system is provided comprising container carriers and a track with a transport mechanism for moving the container carriers along a transportation lane. The transport mechanism defines a transport plane along which the container carriers move. A reader device reads the identifying information from the RFID tags. The reader device comprising a reader antenna above the transport plane to generate and emit a reader field for wireless communication with the RFID tag's antenna.

19 Claims, 9 Drawing Sheets

(58) Field of Classification Search
CPC . G01N 2035/00742; G01N 2035/0406; G01N 35/00871; G01N 2035/0477; G01N 2035/0491; G16H 50/20; B01L 3/5453; B01L 2300/022; B01L 2300/023; B01L 2300/0832; B01L 9/06
See application file for complete search history.

(56) References Cited

U.S. PATENT DOCUMENTS

| | | |
|---|---|---|
| 2006/0190185 A1 | 8/2006 | Ford et al. |
| 2007/0110617 A1 | 5/2007 | Nagai et al. |
| 2014/0234065 A1* | 8/2014 | Heise ............... B65G 54/02 |
| | | 414/749.2 |
| 2018/0238920 A1* | 8/2018 | Yaginuma ............. G16H 10/40 |
| 2019/0285660 A1 | 9/2019 | Kopp et al. |

FOREIGN PATENT DOCUMENTS

| | | |
|---|---|---|
| EP | 2589967 A1 | 5/2013 |
| JP | 2007-156953 A | 6/2007 |
| JP | 2014-190864 A | 10/2014 |
| WO | 2010/004332 A1 | 1/2010 |
| WO | 2010/038333 A1 | 4/2010 |
| WO | 2010/086596 A1 | 8/2010 |
| WO | 2013/064662 A1 | 5/2013 |
| WO | 2013/064665 A1 | 5/2013 |
| WO | 2013/099647 A1 | 7/2013 |
| WO | 2016/025606 A1 | 2/2016 |

* cited by examiner

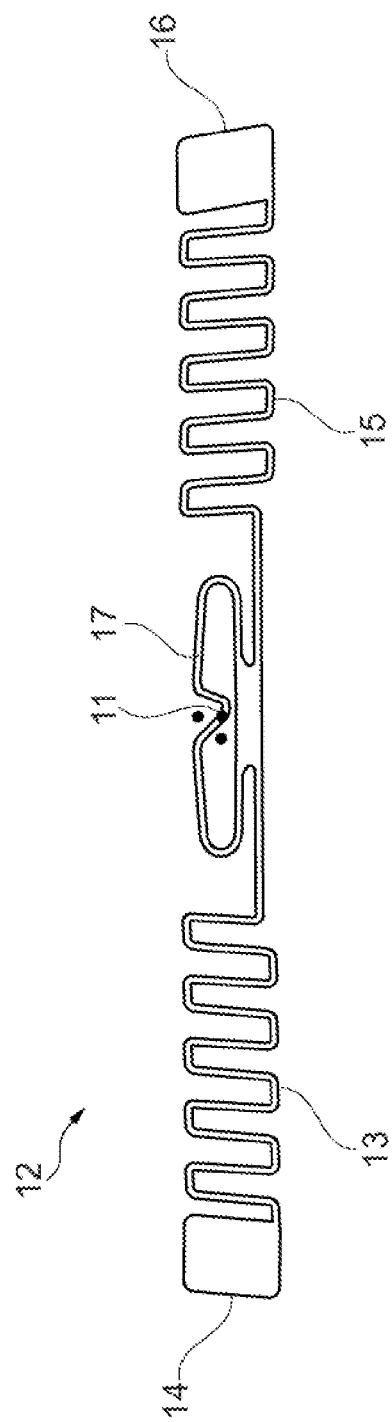

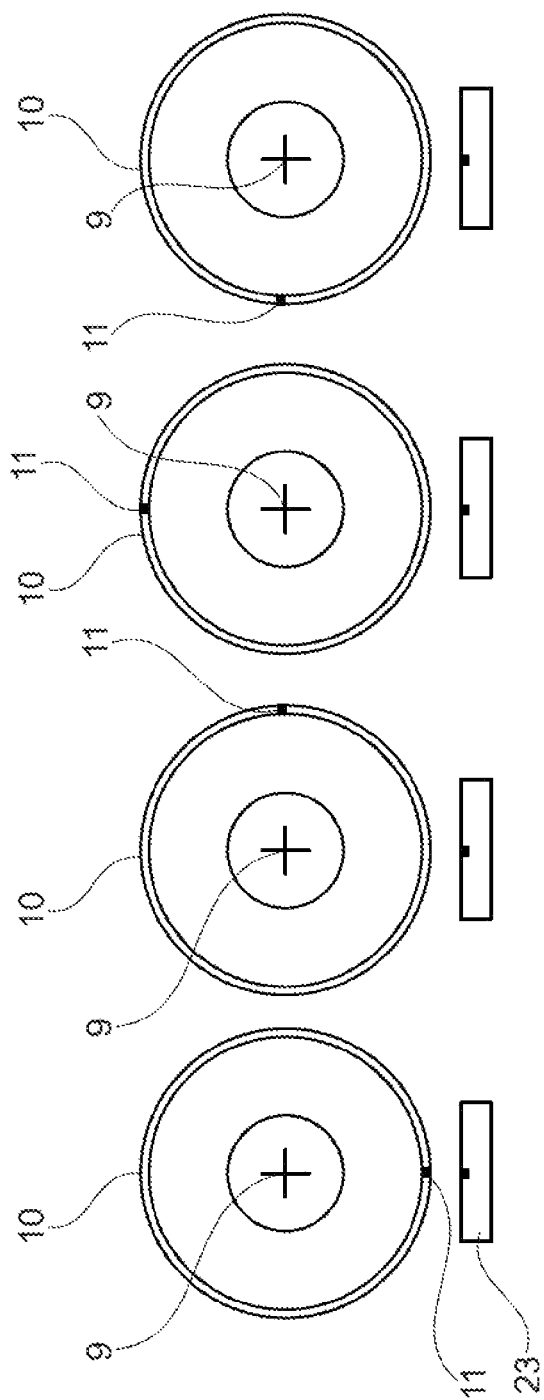

Fig. 9A       Fig. 9B

SAMPLE CONTAINER CARRIER WITH DATA CARRIER FOR AN IN-VITRO DIAGNOSTICS SYSTEM

CROSS-REFERENCE TO RELATED APPLICATIONS

This application claims priority to EP 19204997.1, filed Oct. 24, 2019, which is hereby incorporated by reference.

BACKGROUND

The present disclosure generally relates to a sample container carrier for carrying a sample container along an automation track in an in-vitro diagnostics system, an arrangement for an in-vitro diagnostics system and a method for operating the same.

In-vitro diagnostics systems are applied to test samples such as blood or tissue samples that have been taken from the human body. In-vitro diagnostics can detect diseases or other conditions and can be used to monitor a person's overall health to help cure, treat, or prevent diseases. In-vitro diagnostics also may be applied in precision medicine to identify patients who are likely to benefit from specific treatments or therapies. Some in-vitro diagnostics tests are used in laboratory or other health professional settings.

The (typically liquid) samples are contained in or inserted into sample containers, such as tubes or other vessels. For handling the sample containers, sample container carriers (SCC), such as tube sample holders (TSH) are provided to carry one or more of the sample containers with the test samples, e.g., for moving the sample containers along transportation lanes of the automation track by the carriers. The sample container carriers may have a holding portion for receiving and holding the sample containers, e.g., by a suitable opening, a clamping mechanism, and the like, and may have a base portion for supporting the sample container carriers on a plane, interacting with a transport mechanism of the automation track and so on. The base portion may comprise a metallic structure to interact with an electromagnetic arrangement of a transport mechanism to move the sample container carriers by magnetic forces, including magnetic levitation. The base may also be sized and shaped to engage a respective conveyer mechanism.

The sample container carriers usually have an identification element such as a bar code or a radio frequency identification (RFID) tag, which includes identification information to identify the sample container carrier, the sample container, the test sample included in the carried container or other information, which allows identification or assignment. The identification information may be a unique identification (ID), which can be read by suitable reading devices. An RFID tag may be arranged in the base portion, wherein reader antennas of the reading device are included in or below the transport plane to establish a wireless data communication connection with the RFID tags. However, metallic structures of the base portion or an electromagnetic arrangement may disturb the magnetic field, which is used for supplying energy to and reading the RFID tags. Furthermore, as the sample container carriers move along the transportation lane, their closed loop antenna used for inductive coupling runs through different phases in which it may be fully, partially or not at all placed in the reading field of the reader antennas. Further, particularly in arrangements in which the sample container carriers are free floating along a transport lane of the automation track, the orientation of the sample container carriers is unknown also leading to a relatively high failure rate in reading the identification information, Therefore, there is a need for a sample container carrier for carrying a sample container along an automation track in an in-vitro diagnostics system, an arrangement for an in-vitro diagnostics system and a method for operating the same, which provide reliable reading of identifying electronic information from a data carrier on the sample container carrier during transport along the automation track

SUMMARY

According to the present disclosure, a sample container carrier for carrying a sample container along an automation track in an in-vitro diagnostics system is presented. The sample container carrier can comprise a holding portion for receiving and holding a sample container. The holding portion can define a top of the sample container carrier. The sample container carrier can also comprise a base portion supporting the holding portion and defining a bottom of the sample container carrier. The base portion can comprise a metallic material or a permanent magnet configured to interact with a dynamic magnetic field generated by an electromagnetic arrangement of a transport mechanism of an automation track for moving the sample container carrier along a transportation lane in a transport plane by magnetic forces. The sample container carrier can also comprise a data carrier containing identifying electronic information. The data carrier can comprise an antenna for wireless data communication with a reader device of the in-vitro diagnostics system to read the identifying information. The data carrier can be arranged on the holding portion adjacent to the top of the sample container carrier with the antenna extending in a direction along an outer circumference of the holding portion.

In accordance with one embodiment of the present disclosure, an arrangement for an in-vitro diagnostics system is presented. The arrangement can comprise a plurality of the above sample container carriers and an automation track comprising a transport mechanism for moving the plurality of sample container carriers along at least one transportation lane. The transport mechanism can define a transport plane along which the plurality of sample container carriers are movable. The transport mechanism can comprise an electromagnetic arrangement that is configured to generate a dynamic magnetic field to interact with the base portions of the sample container carriers for moving the sample container carriers along the transportation lane by magnetic forces. The arrangement can also comprise at least one reader device configured to read the identifying information from the data carriers of the sample container carriers. The reader device can comprise at least one reader antenna configured to generate and emit a reader field for wireless data communication with the antenna of the data carriers of the sample container carriers. The at least one reader antenna can be disposed above the transport plane.

In accordance with another embodiment of the present disclosure, a method for operating an arrangement in an in-vitro diagnostics system is presented. The method can comprise providing an above arrangement, operating the at least one reader device to generate and emit a reading field by the at least one reader antenna, operating the transport mechanism to move at least one of the plurality of sample container carriers along a transportation lane such that the antenna of the data carrier of the sample container carrier is brought into the reading field emitted by the at least one reader antenna to establish a wireless data communication connection between the data carrier and the reader device, and operating the at least one reader device to read the identifying information from the data carrier via the established data communication connection.

Accordingly, it is a feature of the embodiments of the present disclosure to provide for a sample container carrier for carrying a sample container along an automation track in an in-vitro diagnostics system, an arrangement for an in-vitro diagnostics system and a method for operating the same, which provide reliable reading of identifying electronic information from a data carrier on the sample container carrier during transport along the automation track. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 3 illustrates an exemplary embodiment of an RFID tag according to an embodiment of the present disclosure.

FIGS. 6A-6D illustrate schematic representations of a sample container carrier disposed near a reader antenna in different orientations according to an embodiment of the present disclosure.

FIGS. 9A-9B illustrate+− schematic representations of different embodiments of an RFID reader arrangement according to an embodiment of the present disclosure.

DETAILED DESCRIPTION

Figure 1B:
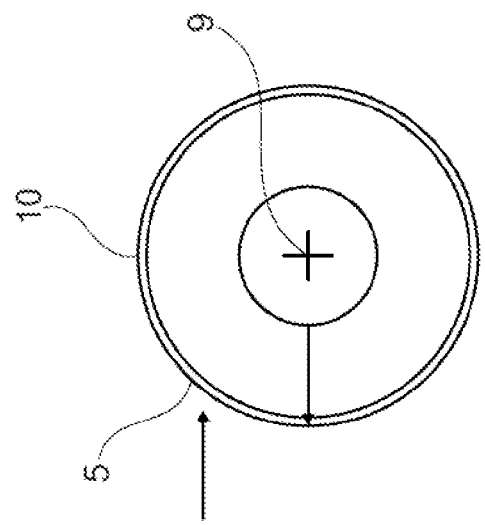
FIGS. 1A-1B illustrate a schematic representation of a sample container carrier in different views according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sample container carrier for carrying a sample container along an automation track in an in-vitro diagnostics system is provided. The sample container carrier (hereinafter also referred to as "SCC" or simply "carrier") can comprise a holding portion for receiving and holding a sample container and a base portion for supporting the holding portion. The sample container carrier can further comprise a data carrier containing identifying information. The data carrier can comprise an antenna for wireless data communication with a reader device. The data carrier can be arranged on the holding portion.

The identifying information may include identifying information about at least one of the sample container carrier, the sample container and a sample contained in the sample container, or other information allowing identification or assignment as desired or necessary to track the sample container carriers as they go through the automation track. The holding portion may for example have an opening or cavity to receive a sample container, such as a tube. Methods for retaining, clamping or tightening the container in the holding portion may be provided. The base portion may serve as or may include a coupling portion configured to couple with a transport mechanism of the automation systems as will be exemplarily described in more detail below.

An arrangement for an in-vitro diagnostics system is provided. The arrangement can comprise at least one, and in some embodiments, a plurality, of the sample container carriers described above and hereinafter and an automation track with a transport mechanism for moving the sample container carriers along at least one transportation lane, wherein the transport mechanism can define a transport plane along which the plurality of sample container carriers are movable. For instance, the transport plane may be a surface of a transport module or a conveyor belt. Generally, the transport plane may be defined as a plane in which the lower end surfaces of the sample container carriers move during transport. The arrangement can further comprise at least one reader device configured to read the identifying electronic information from the data carrier of the sample container carrier, the reader device comprising at least one reader antenna configured to generate and emit a reader field for wireless data communication with the antenna of the data carrier of the sample container carrier. The at least one reader antenna can be disposed above the transport plane. In one embodiment, the at least one reader antenna can be disposed above the transport plane and along the transportation lane such that the data carrier of the sample container carrier(s) can be brought into the reading field while they are moved along the transportation lane.

A method for operating an arrangement in an in-vitro diagnostics system is provided. The arrangement as described above and hereinafter, and in some embodiments, including a plurality of the described sample container carriers can be provided or set up. The method can comprise the following steps for operating the arrangement, particularly with respect to reading the data carrier during transport of the sample container carrier(s). The at least one reader device can be operated to generate and emit a reading field by the at least one reader antenna. The transport mechanism can be operated to move at least one of the plurality of sample container carriers along a transportation lane such that the antenna of the data carrier of the sample container carrier can be brought into the reading field emitted by the at least one reader antenna to establish a wireless data communication connection between the data carrier and the reader device. The at least one reader device can be operated to read the identifying electronic information from the data carrier via the established data communication connection.

Since the data carrier of a sample container carrier can be arranged in the holding portion rather than in the base portion, reading of the data carrier can be improved because data carrier can be spaced apart from the base portion and the reading field does not interfere with the transport mechanism below the carriers and respective coupling structures in the base portion that are provided to interact with the transport mechanism. In other words, reading the data carriers can be made independent from the transport mechanism.

In an example, the data carrier may be provided with a radio frequency identification (RFID) tag. For the data carrier, one or more antennas may be provided.

The base portion can define a bottom or lower end of the sample container carrier and the holding portion can define a top or upper end of the sample container carrier. The data carrier can be disposed adjacent to the top of the sample container carrier, alternatively at an upper edge of the carrier. In other words, the data carrier can be alternatively disposed at a height of the carrier close to, at or even overlapping the upper edge of the carrier. This position of the data carrier can provide a maximum distance of the data carrier from the bottom of the sample container carrier (in an axial or vertical direction) and, thus, from possible disturbing structures of a transport mechanism.

The antenna of the data carrier can extend in a direction along an outer circumference of the holding portion, which direction may extend in a plane, which can be substantially parallel to a plane defined by the bottom of the sample container carrier. The (at least one) antenna may be disposed on an outer circumferential surface of the holding portion. Placing the data carrier on the outer circumferential surface can provide a maximum distance from a center of the carrier (in a radial direction) and, thus, a maximal distance from the sample container. Since the sample in the sample container is usually liquid, placing the data carrier away from the liquid sample can further reduce disturbing effects of the liquid such that reading the data carrier can be further improved. In one embodiment, the holding portion may comprise a holder for receiving and holding a sample container disposed in a center of the holding portion such that the data carrier can be spaced apart in a radial direction from a sample container received in the holder. For instance, the holder may be a central hole accessible from the top, such a wall thickness between the hole and the outer circumference of the holding portion can define a radial distance of the data carrier from the sample container. It can be appreciated that other ways of holding such as, for example, clamp holders or the like, may be provided for receiving and holding a sample container.

Advantageously, at least the holding portion can have a substantially cylindrical (outer) shape such that the antenna can be arranged in a substantially circular plane defined by the outer circumferential surface of the substantially cylindrical holding portion. This rotationally symmetric shape can reduce effects of the angular orientation. The sample container carrier may be configured to receive and hold only a single sample container such that a sample can be uniquely identified by a clearly assigned data carrier on the respective sample container carrier carrying the sample container with the sample.

The data carrier may include an integrated circuit (IC) (i.e., the "chip") having stored the identifying electronic information. The antenna may comprise a first portion with a first open end and a second portion with a second open end. The first and second portions can extend in directions away from the IC of the data carrier or, alternatively, in opposing directions.

The data carrier may extend substantially around the entire circumference of the holding portion, i.e., along the outer circumference of the holding portion by at least 90%, alternatively, at least 95%, or in another alternative 98% or 99%. The first and second free ends can face each other but can be spaced apart by a gap or other insulators. In other words, while the first and second ends of the antenna may be in close proximity to each other, they do not contact each other and the antenna will not form a closed ring. By providing the data carrier with an antenna that covers substantially the entire circumference of the sample container carrier, some RFID detection may be substantially independent of the orientation of the carriers during transport. In one embodiment, in free-floating transport mechanisms such as, for example, magnetic levitation, but also on conveyor belts where the carriers are not secured in a certain orientation, the carriers can rotate arbitrarily around their central axis during transport. If the data carriers were small and disposed only on one side of the carriers, reading the data carrier would fail if the data carrier faces away from the antenna because of too low signal strength. The elongate antenna around the circumference of the carrier can allow for reading the data carrier in any orientation of 360 degrees.

The antenna of the data carrier may comprise an (electric) dipole antenna. The dipole antenna, in contrast to closed loop antennas, can be configured to receive an electric field. Its first and second portions may extend symmetrically from the IC of the data carrier. The dipole antenna may be arranged in a meander shape with a height that can be small compared to length of the antenna from one free end to the other. This shape can allow for easy placement of the data carrier in the upper region of the holding portion. Accordingly, the at least one reader antenna may be configured to generate and emit an electric field, the electric field having alternatively a frequency in the ultra-high frequency range such as, for example, having a frequency of at least 850 MHz. The data carrier may then be referred to as "UHF tag", which can be understood as a type of RFID tag. The wavelength can be in the order of magnitude of dimensions of sample container carrier (decimeter range). In one embodiment, compared to a magnetic field (H-field) used for inductive coupling of common data carriers with closed loop or ring-shaped antennas, less energy may be necessary due to the better efficiency of the electric field (E-field). The ultra-high frequency (UHF) can also provide a higher date rate compared to high frequency (HF) or low frequency (LF).

The at least one antenna of the data carrier may further comprises a central portion extending from the IC of the data carrier in a closed loop. The closed loop central portion may be arranged between the first and second portions of the dipole antenna and may be configured to receive a magnetic field. This may be used for short-distance inductive coupling. More specifically, the closed loop antenna may be provided in addition to the aforementioned dipole antenna. In other words, the UHF-tag may be provided with an additional antenna for also allowing communication in the short distance range by a magnetic field.

At least a portion of the holding portion may be made of a non-metallic material, more specifically; the portion of the holding portion on which the data carrier is arranged may be made of a non-metallic material to avoid disturbing effects, which can be caused by metallic materials.

In an embodiment, the base portion can comprise a metallic material or a permanent magnet. For instance, a metallic bottom plate, or other metallic or magnetic structure, may be provided in the base portion to allow transport by magnetic forces, including magnetic levitation. The transport mechanism can comprise an electromagnetic arrangement that can be configured to generate a dynamic magnetic field to interact with the base portions of the sample container carriers for moving the sample container carriers along the transportation lane by magnetic forces. Due to the arrangement of the data carriers close to the top of the carriers and the respective arrangement of the reader antennas above the transport plane, the reader field can be above the transport plane and, thus, does not interfere with the magnetic field of the transport mechanism. Likewise, in case of other transport mechanisms, the reader field may not interfere with the transport mechanism.

In one embodiment, the at least one reader antenna may be disposed above the transport plane at a vertical distance from the transport plane to be aligned with the antennas of the data carriers. In other words, the reader field generated and emitted by the at least one antenna can be aligned with the data carriers of the sample container carriers, which can mean that the reader field can be targeted to the data carriers to achieve a maximum signal strength during wireless communication. In one embodiment, in combination with the antennas of the data carriers extending in a plane substantially parallel to the bottom of the sample container carriers, i.e., substantially parallel to the transport plane, the alignment of the reader antenna and the data carrier antennas can be independent from the rotational orientation of the sample container carriers.

The arrangement may comprise at least two reader antennas arranged on opposing sides of the transportation lane or a plurality of reader antennas arranged on one side or opposing sides of a transportation lane. It may be envisioned to provide multiple substantially parallel transportation lanes. A plurality of reader antennas can be arranged to form "gates" of the transportation lanes for reading the data carriers when they pass through the "gates." While the elongate antenna around the circumference of the holding portion already makes the reading substantially independent from the angular orientation of the sample container carriers, providing reader antennas on opposing sides of a transportation lane can further improve the reading. The at least one reader device may be operated to generate and emit a reading field by the at least two reader antennas. The transport mechanism may be operated to move the sample container carrier along the transportation lane between the at least two reader antennas such that at least one antenna of the data carrier can be brought into the reading field generated and emitted by the at least two reader antennas to establish a data communication connection between the data carrier and the reader device. The identifying information may then be read from the data carrier by at least one of the reader antennas, alternatively, by at least two of the reader antennas on opposing sides of the transportation lane. The reading may take place by a selected one of the reader antennas or by all reader antennas, and may depend on the orientation of the carriers and distances from the antennas. A respective control device may be provided to control the antennas and process the reading signals.

A sample container carrier for carrying a sample container along an automation track in an in-vitro diagnostics system is provided. The sample container carrier can comprise a holding portion for receiving and holding a sample container and a base portion for supporting the holding portion. The sample container carrier can further comprise a data carrier containing identifying electronic information. The data carrier can comprise an antenna device for wireless data communication with a reader device. The antenna device can comprise a dipole antenna.

The embodiments disclosed with respect to the sample container carrier above may apply to the arrangement and method for operating the arrangement mutatis mutandis. Likewise, the embodiments disclosed with respect to the arrangement above may apply to the method for operating the arrangement mutatis mutandis and vice versa.

Figure 1A:
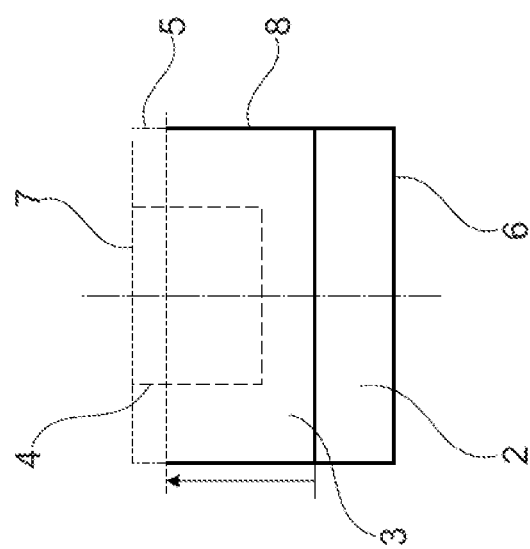

Referring initially to FIG. 1, FIG. 1 shows different schematic views of a sample container carrier 1 ("SCC"), which may also be referred to as tube sample holder particularly if the sample container is in the form of a tube. The SCC 1 can have a base portion 2 such as, for example, a metallic base portion 2 to interact with a magnet transportation mechanism as will be described below in more detail. Such transport mechanism which can use magnetic levitation is known e.g., from WO 2013/064662 A1, which is incorporated herein by reference. The SCC 1 can have a holding portion 3 made of a plastic material and having a holder for holding a sample container (container not shown in FIG. 1) such as, for example, a hole 4 for receiving a tube with a liquid test sample in an upright position (also indicated by dashed line in the side view shown in FIG. 1a). Any holder for securely holding the tube may be provided, e.g., a clamping mechanism or the like, or the tube may simply held by form fit or press fit.

A data carrier in the form of an radio frequency identification (RFID) tag 5 can be placed or wrapped around the circumferential surface 8 of the holding portion 3 at the upper edge 7, i.e., at a maximum distance from the bottom edge 6. Thereby, influences of the metallic base portion 2 on the RFID tag 5 can be avoided or at least reduced to a minimum. At the same time, the RFID tag 5 can be placed at a maximum distance from the central axis 9 of the holding portion 2 and thus at a maximum distance from the sample container to reduce influences of a liquid test sample contained in the sample container. The RFID tag 5 can extend almost completely around the circumference, i.e., about 95% to 99% of the circumference and can leave only a small gap 10 to avoid a ring closure.

Figure 2:
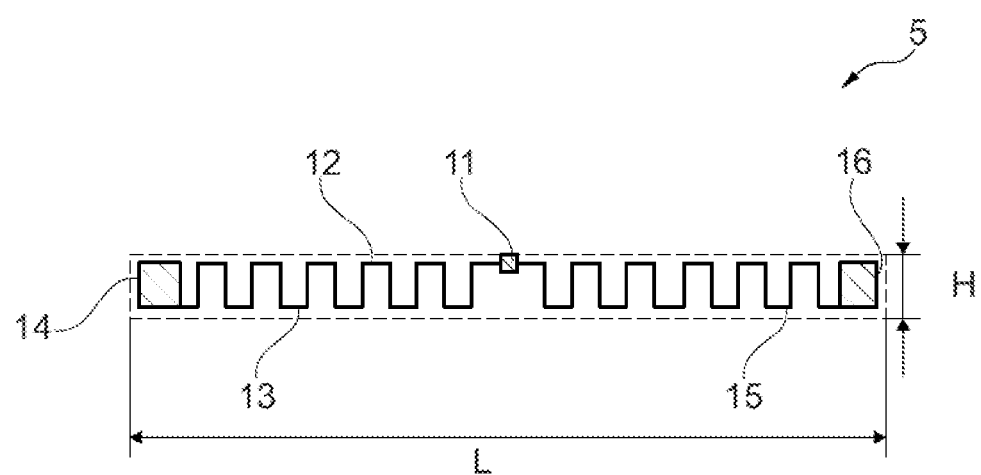
FIG. 2 illustrates a schematic representation of a data carrier provided as an RFID tag according to an embodiment of the present disclosure.

A schematic representation of an RFID tag 5 is shown in FIG. 2. The RFID tag 5 can have an RFID IC 11 (integrated circuit or chip) in the center. The RFID tag 5 can further comprise a dipole antenna 12 having a first portion 13 with a free end 14 and a second portion 15 with a free end 16 extending symmetrically in opposing directions from the RFID IC 11. When attached to a SCC 1, the aforementioned gap 10 can be between the free ends 14 and 16. The length L of the RFID tag 5 can be selected to cover almost the entire circumference of the holding portion 3 as described above. The height H of the RFID tag can be small to achieve a maximum distance of the lower edge of the RFID tag 5 from the upper edge of the base portion 2.

FIG. 3 shows an exemplary embodiment of an RFID tag 5 as described above. In this embodiment, an additional magnetic loop antenna 17 can be provided between the portions 13 and 15 of the dipole antenna 12. The length of the electric dipole antenna 12 can be configured to the electric field and the circumference of the SCC 1. The RFID tag 5 may be provided as a flat label or circular sleeve to be attached to the SCC 1, e.g. by adhesive, or may be integrated in the holding portion 3 of the SCC 1 (on or close the outer circumferential surface 8). It can be appreciated that an integrated or embedded tag may be advantageous when it comes to cleaning and possibly sterilization of the SCC 1, while a separate attachable and removable tag may provide more flexibility and allows replacing, e.g., when the tag is broken.

Figure 4B:
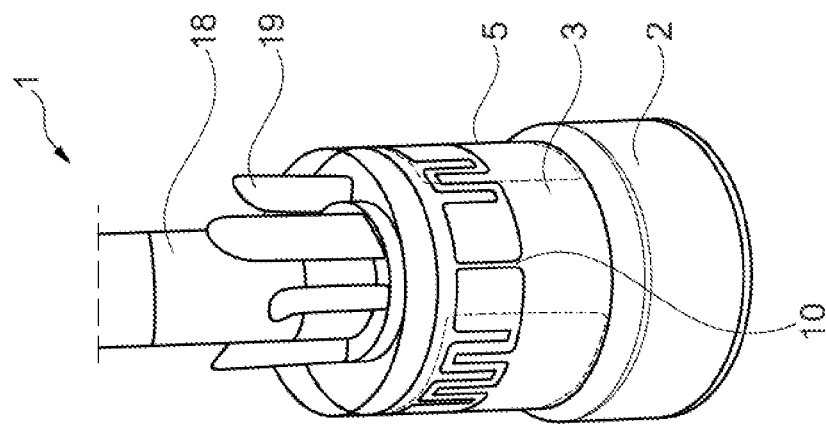
FIGS. 4A-4B illustrate an exemplary embodiment of a sample container carrier with a sample container in different views according to an embodiment of the present disclosure.
Figure 4A:
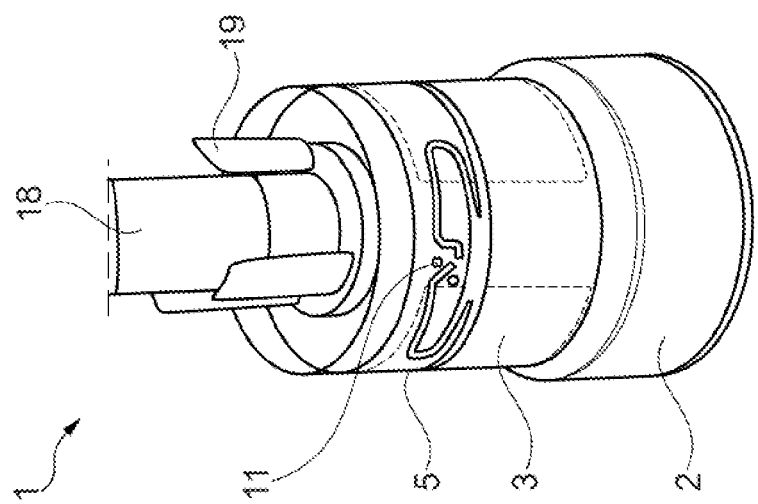

FIG. 4 shows two different views of an exemplary embodiment of a SCC 1 with an RFID tag 5 attached and a sample container 18 held in the holding portion 3. Here, additional holding structures 19 can extend from the holding portion to hold the sample container 18. As can be seen in FIG. 4, a carrier film of the RFID tag 5 can extend above beyond the holding portion 3 to place the antenna 12 at a maximum distance from the metal base portion 2.

Figure 5:
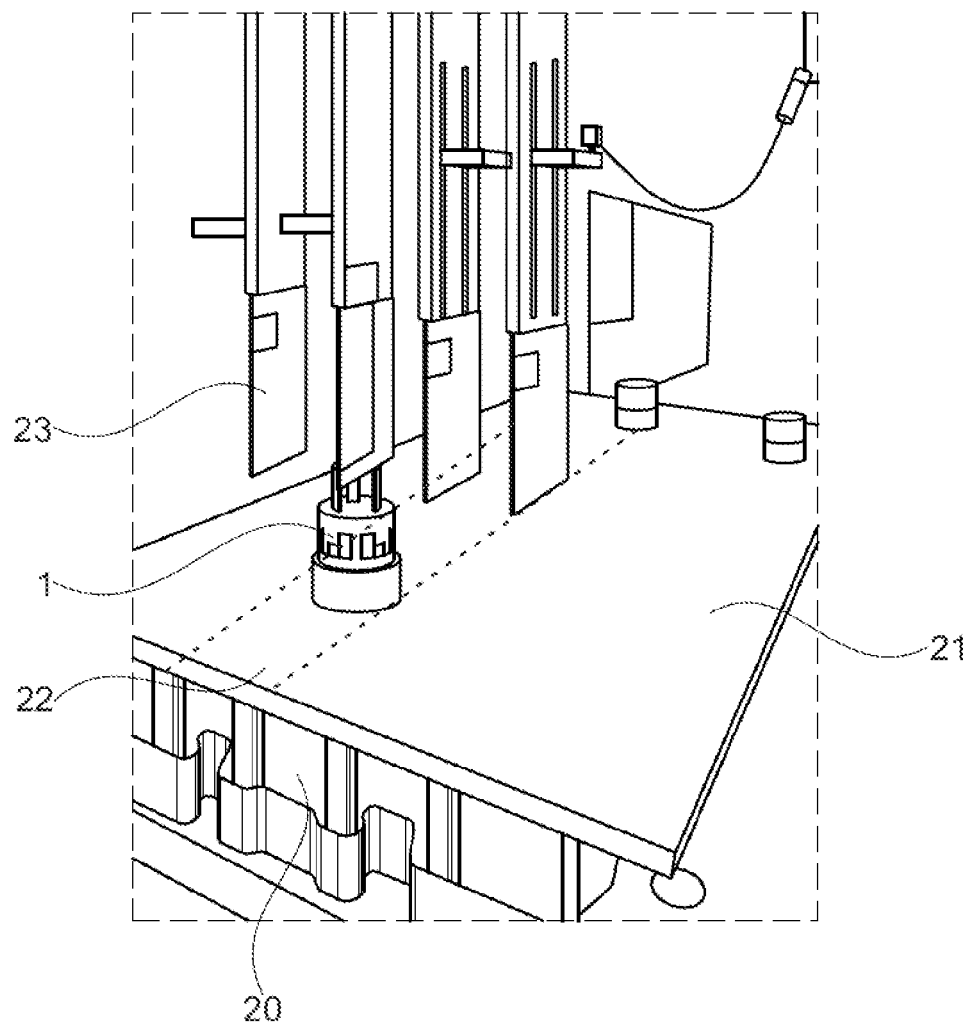
FIG. 5 illustrates an exemplary embodiment of an arrangement for an in-vitro diagnostics system according to an embodiment of the present disclosure.

FIG. 5 shows an embodiment of an arrangement of an automation track for an in-vitro diagnostics system. The automation track, for example, may be provided in an in-vitro diagnostics system applied to test samples such as blood that have been taken from the human body. The in-vitro diagnostics tests may be used in laboratory or other health professional settings.

The automation track can be provided with a transport mechanism 20 that can be configured to move the carriers 1 along transportation lanes 23 (indicated by dashed lines). The transport mechanism 20 may generate a dynamic magnetic field for moving the carriers 1 by magnetic forces. Contactless movement may be achieved by magnetic levitation. The carriers 1 can move in a transport plane 21. By moving the carriers 1 along the automation track, the carriers 1 may be moved to different handling or operation stations (not shown) of the in-vitro diagnostics system. In the different handling or operation stations, a plurality of application steps may be applied to the samples. For example, an optical analysis may be applied to a sample provided in one of the sample containers 18. Different arrangements for in-vitro diagnostics systems provided with an automation track are known as such.

In order to read the identifying information from the RFID tags 5, multiple reader antennas 23 can be provided above the transport plane 21. They can generate and emit an electric field to energize the dipole antenna 12 of the RFID tags 5. In order to be able to move the RFID tags 5 into the emitted reading field, the reader antennas 23 can be arranged at a height above the transport plane 21 corresponding to the respective height of the RFID tags 5. Multiple reader antennas 23 can be placed on opposing sides of multiple transportation lanes 22. This can allow parallel processing of multiple samples at the same time.

Due to the free floating transport of the carriers 1, i.e., because the carriers 1 are not locked to the transport mechanism 20 by respective (mechanical) engagement but are magnetically coupled to the transport mechanism 20, they may rotate around their central axis 8 during movement along the transportation lanes 22. Different exemplary angular orientations (0°, 90°, 180°, 270°) relative to a reader antenna 23 are shown in FIGS. 6 a), b), c), d). Due to the circumferential extension of the RFID tag 5, more specifically the dipole antenna 12 leaving only a small gap 10 (diametrically opposite the RFID IC 11 because of the symmetry), a sufficient wireless data communication connection can be established independent from the orientation of the carriers 1 (cf. also FIG. 10).

Figure 7A:
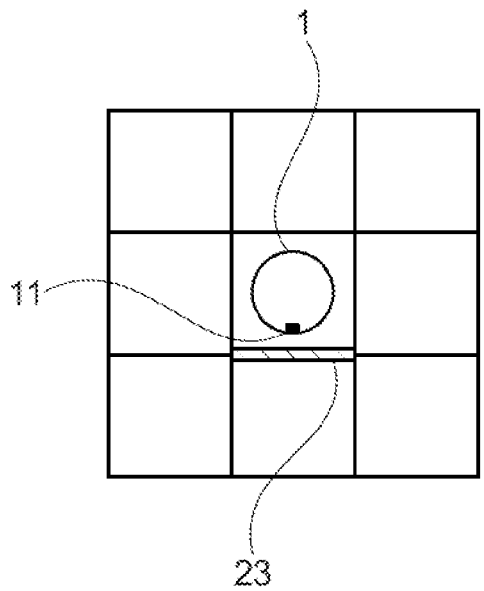
FIGS. 7A-7B illustrate schematic representations of a sample container carrier in different read positions according to an embodiment of the present disclosure.
Figure 7B:
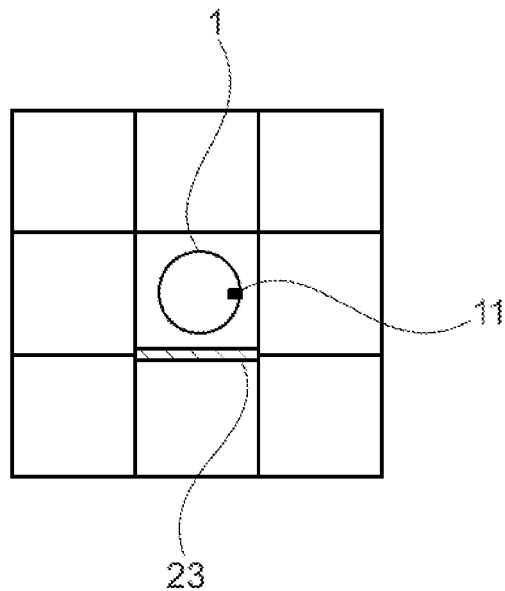
Figure 8A:
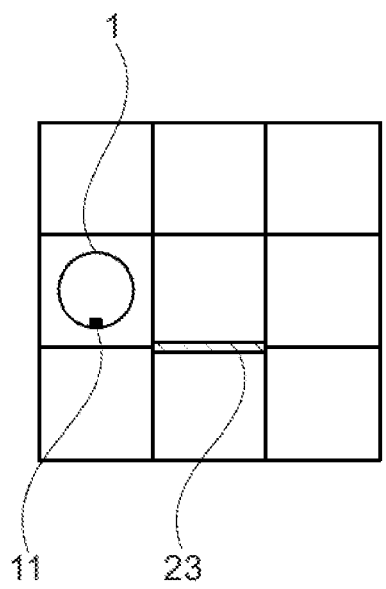
FIGS. 8A-8B illustrate schematic representations of a sample container carrier in different non-read positions according to an embodiment of the present disclosure.
Figure 8B:
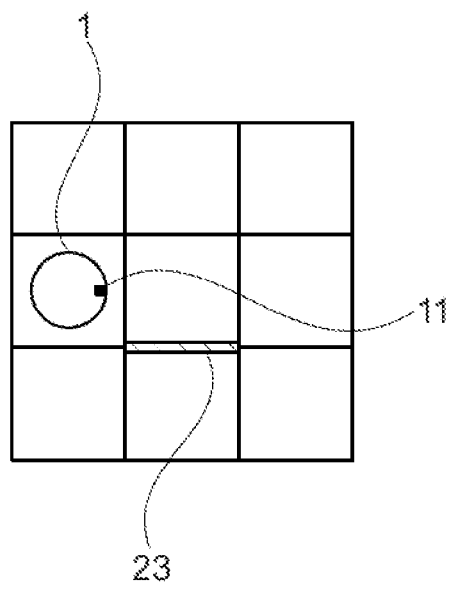
Figures 9A, 9B:
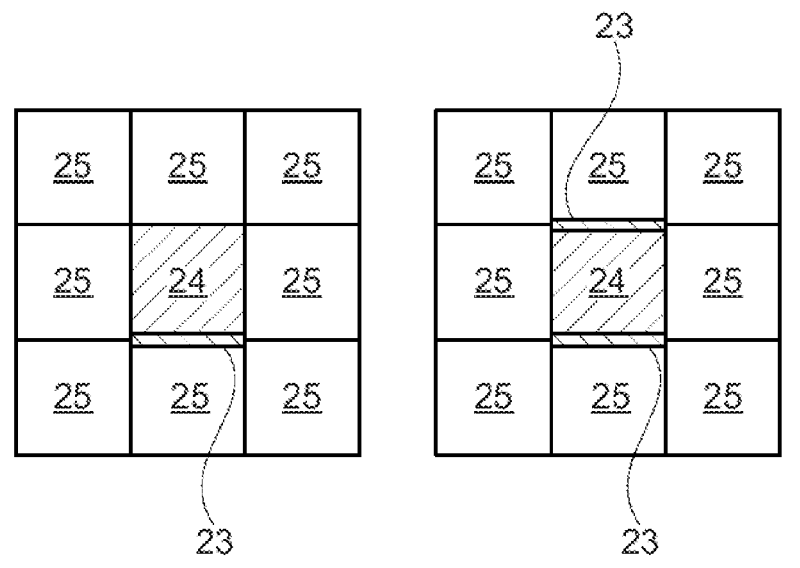

Thus, when the carriers 1 pass the reader antennas 23, they can always be in a "read position" with sufficient signal strength for successful reading the information from the RFID tag 5 (see FIG. 7). Likewise, when the carriers 1 are outside the range of the antennas 23, no unintentional reading of the RFID tags 5 can take place (see FIG. 8). See also designated "read zones" 24 and "non-read zones" 25 in FIG. 9 shown for an embodiment with one reader antenna 23 (FIG. 9a) and two reader antennas (FIG. 9b).

Figure 10:
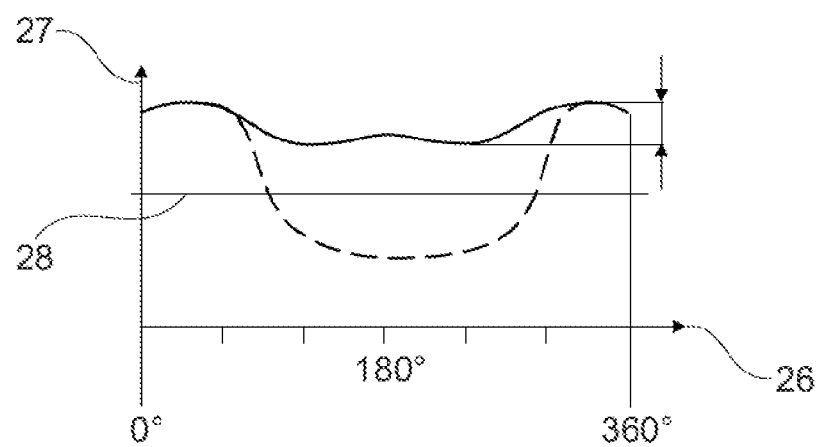
FIG. 10 illustrates a diagram illustrating the signal strength during RFID reading depending on the orientation of the sample container carrier according to an embodiment of the present disclosure.

FIG. 10 schematically illustrates the signal strength (y-axis 27) depending on the angular orientation of a carrier 1 (x-axis 26) showing that the signal strength can always be above a minimum signal strength 28 required for detection of the RFID tag, i.e., successful reading, independent from the angular orientation (provided that the carrier 1 is in a read zone 24). The signal strength can vary only in a small range. In contrast to what is shown in dashed lines, the signal strength for another RFID tag, e.g., which is too short compared to the circumference. It can be seen that the signal strength can fall below the minimum signal strength when the RFID tag faces away from the reader antenna (indicated exemplarily for a rotational range from about 90° to about 270°).

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A sample container carrier for carrying a sample container along an automation track in an in-vitro diagnostics system, the sample container carrier comprising:
   a holding portion for receiving and holding a sample container, the holding portion defining a top of the sample container carrier;
   a base portion supporting the holding portion and defining a bottom of the sample container carrier, wherein the base portion comprises a metallic material or a permanent magnet configured to interact with a dynamic magnetic field generated by an electromagnetic arrangement of a transport mechanism of an automation track for moving the sample container carrier along a transportation lane in a transport plane by magnetic forces; and
   a data carrier containing identifying electronic information, the data carrier comprising an antenna for wireless data communication with a reader device of the in-vitro diagnostics system to read the identifying information, wherein the data carrier is arranged on the holding portion adjacent to the top of the sample container carrier with the antenna extending in a direction along an outer circumference of the holding portion.

2. The sample container carrier of claim 1, wherein the direction in which the antenna extends along the outer circumference of the holding portion extends in a plane, which is parallel to a plane defined by the bottom of the sample container carrier.

3. The sample container carrier of claim 1, wherein the holding portion comprises a holder for receiving and holding a sample container, wherein the holder is disposed in a center of the holding portion such that the data carrier is spaced apart in a radial direction from a sample container received in the holder.

4. The sample container carrier of claim 1, wherein the holding portion has a cylindrical shape such that the antenna is arranged in a circular plane defined by the outer circumferential surface of the holding portion.

5. The sample container carrier of claim 1, wherein the data carrier comprises an integrated circuit (IC) having stored the identifying electronic information and wherein the antenna comprises a first portion with a first open end and a second portion with a second open end, wherein the first and second portions extend in directions away from the IC of the data carrier.

6. The sample container carrier of claim 5, wherein the data carrier extends along the outer circumference of the holding portion by at least 90% of the outer circumferential length such that the first and second free ends face each other spaced apart by a gap.

7. The sample container carrier of claim 5, wherein the data carrier extends along the outer circumference of the holding portion by at least 95% of the outer circumferential length such that the first and second free ends face each other spaced apart by a gap.

8. The sample container carrier of claim 5, wherein the data carrier extends along the outer circumference of the holding portion by 99% of the outer circumferential length such that the first and second free ends face each other spaced apart by a gap.

9. The sample container carrier of claim 1, wherein the antenna of the data carrier comprises a dipole antenna.

10. The sample container carrier of claim 1, wherein the data carrier includes an integrated circuit (IC) having stored the identifying electronic information and wherein the antenna further comprises a central portion extending from the IC in a closed loop.

11. The sample container carrier of claim 1, wherein at least a portion of the holding portion on which the data carrier is arranged is made of a non-metallic material.

12. An arrangement for an in-vitro diagnostics system, the arrangement comprising:
a plurality of sample container carriers according to claim 1;
an automation track comprising a transport mechanism for moving the plurality of sample container carriers along at least one transportation lane, the transport mechanism defining a transport plane along which the plurality of sample container carriers are movable, wherein the transport mechanism comprises an electromagnetic arrangement that is configured to generate a dynamic magnetic field to interact with the base portions of the sample container carriers for moving the sample container carriers along the transportation lane by magnetic forces; and
at least one reader device configured to read the identifying information from the data carriers of the sample container carriers, the at least one reader device comprising at least one reader antenna configured to generate and emit a reader field for wireless data communication with the antenna of the data carriers of the sample container carriers, the at least one reader antenna disposed above the transport plane.

13. The arrangement of claim 12, wherein the at least one reader antenna is configured to generate and emit an electric field, the electric field having a frequency in the ultra-high frequency (UHF) range.

14. The arrangement of claim 13, wherein the electric field has a frequency of at least 850 MHz.

15. The arrangement of claim 12, wherein the at least one reader antenna comprises at least two reader antennas arranged on opposing sides of the transportation lane.

16. The arrangement of claim 12, wherein the at least one reader antenna is disposed above the transport plane at a vertical distance from the transport plane so as to be aligned with the antenna of the data carriers of the sample container carriers.

17. A method for operating an arrangement in an in-vitro diagnostics system, the method comprising:
providing an arrangement according to claim 12;
operating the at least one reader device to generate and emit a reading field by the at least one reader antenna;
operating the transport mechanism to move at least one of the plurality of sample container carriers along a transportation lane such that the antenna of the data carrier of the at least one sample container carrier of the plurality of sample container carriers is brought into the reading field emitted by the at least one reader antenna to establish a wireless data communication connection between the data carrier and the at least one reader device; and
operating the at least one reader device to read the identifying information from the data carrier via the established data communication connection.

18. The method of claim 17 wherein the at least one reader device is provided with at least two reader antennas arranged on opposing sides of the transportation lane and wherein the at least one reader device is operated to generate and emit the reading field by the at least two reader antennas.

19. The method of claim 18, wherein the transport mechanism is operated to move the at least one sample container carrier of the plurality of sample container carriers along the transportation lane between the at least two reader antennas such that the antenna of the data carrier is brought into the reading field generated and emitted by the at least two reader antennas to establish a data communication connection between the data carrier and the reader device and wherein the identifying electronic information is read from the data carrier by at least one of the reader antennas.

* * * * *